(12) United States Patent
Larsson et al.

(10) Patent No.: US 7,004,974 B1
(45) Date of Patent: Feb. 28, 2006

(54) MATERIAL FOR BONE RECONSTRUCTION (75) Inventors: Cecilia Larsson, Göteborg (SE);
Helena Ljusberg-Wahren, Höllviken (SE)

(73) Assignee: Nobel Biocare AB (publ.), Gothenburg (SE)

( * ) Notice: Subject to any disclaimer, the term of this patent is extended or adjusted under 35 U.S.C. 154(b) by 0 days.

(21) Appl. No.: 09/743,762

(22) PCT Filed: Jul. 6, 1999

(86) PCT No.: PCT/SE99/01231

§ 371 (c)(1),
(2), (4) Date: May 14, 2001

(87) PCT Pub. No.: WO00/04940

PCT Pub. Date: Feb. 3, 2000

(30)  Foreign Application Priority Data

Jul. 13, 1998  (SE) .................................. 9802529

(51) Int. Cl.
    *A61F 2/28* (2006.01)
(52) U.S. Cl. .................. 623/23.56; 623/16.11; 623/23.51; 623/23.58; 623/23.61; 623/23.75
(58) Field of Classification Search ............. 623/16.11, 623/20.17, 23.57, 23.56, 23.61, 23.51, 23.58, 623/23.63
    See application file for complete search history.

(56)  References Cited

U.S. PATENT DOCUMENTS

| | | | |
|---|---|---|---|
| 4,192,021 A | 3/1980 | Deibig et al. ................... 3/1.9 |
| 5,092,888 A | 3/1992 | Iwamoto et al. .............. 623/16 |
| 5,139,424 A | 8/1992 | Yli-Urpo | |
| 5,196,201 A * | 3/1993 | Larsson et al. ............. 424/422 |
| 5,236,495 A | 8/1993 | Manabe et al. | |
| 5,338,772 A * | 8/1994 | Bauer et al. ............. 428/304.4 |
| 5,769,897 A | 6/1998 | Harle .......................... 623/16 |
| 5,972,366 A * | 10/1999 | Haynes et al. ............. 424/422 |
| 6,280,474 B1 * | 8/2001 | Cassidy et al. ............. 606/232 |

FOREIGN PATENT DOCUMENTS

| | | | |
|---|---|---|---|
| JP | 2198560 | * | 8/1990 |
| JP | 2631890 | | 4/1997 |
| WO | WO 95/34287 | | 12/1995 |

(Continued)

OTHER PUBLICATIONS

Barlow, J.W., et al, Preparation of Calcium Phosphate Implants, *Global Summit*, Annual Meeting, 2000, Global Alliance of Rapid Prototyping Associations (GARPA), 17 pages.

(Continued)

*Primary Examiner*—Corrine McDermott
*Assistant Examiner*—William H Matthews
(74) *Attorney, Agent, or Firm*—Connolly Bove Lodge & Hutz LLP (57)  ABSTRACT The invention relates to a preparation for restoring bone in the body of humans or animals in connection with an existing structure, a bone implant or some other prosthetic construction, as well as a method for restoring bone. The bone restoring preparation consists of an easily handleable and controllable preparation (composition) of resorbable calcium phosphate granules and a carrier of a biopolymer or lipid type. The preparation is intended to be applied in the position where the bone needs to be replaced, reinforced or built up, especially in connection with a bone implant or some other prosthetic construction where there is a lack of sufficient bone volume, or where the quality of the bone is too poor to allow a load-carrying function, for example permanent fixing of an implant.

26 Claims, 5 Drawing Sheets

FOREIGN PATENT DOCUMENTS

| WO | WO 97/45147 | 12/1997 |
| --- | --- | --- |
| WO | WO 00/02597 | 1/2000 |

OTHER PUBLICATIONS

Judy, Kenneth; "Oral Implantology Case Reports"; NYS Dental Journal, Dec. 1986; pp. 24-27.

Nijweide, P.J., et al., Cells of Bone: Proliferation, Differentiation, and Hormonal Regulation, Physiological Reviews, Pub. by The American Physiological Society, vol. 66, No. 4, Oct. 1986, pp. 855-886.

Daculsi, G., et al.; Adaptive Crystal Formation in Normal and Pathological Calcifications in Synthetic Calcium Phosphate and Related Biomaterials; International Review of Cytology, vol. 172; 1997; pp. 129-191.

Marshall, R. Urist, et al.; Lipids Closely Associated with Bone Morphogenetic Protein (BMP) . . . and Induced Heterotopic Bone Formation; Connective Tissue Research, vol. 36(1); pp. 9-20; 1997 OPA (Overseas Publishers Association).

Ricci, J.L., et al.; Evaluation of a Low-Temperature Calcium Phosphate Particulate Implant Material: Physical-Chemical Properties and In Vivo Bone Response; Oral Maxillofac Surg., vol. 50, 1992, pp. 969-978.

Smiler, D.G. , et al.; Sinus Lift Grafts and Endosseous Implants- Treatment of the Atrophic Posterior Maxilla; Dental Clinics of North America; vol. 36, No. 1; Jan. 1992; pp. 151-186.

Wetzel, A.C., et al.; Bone apposition onto oral implants in the sinus area filled with different grafting materials—A histological study in beagle dogs; Clin. Oral Implants Research; 1995; No. 6, pp. 155-163.

Ashley, G.W., et al., (1996), Phosphatidylcholinium compounds: A new class of cationic phospholipids with transfection activity and unusual physical properties. (abstract), Biophysical J. 70: A 88.

Saito, Akira, et al.; Bone Morphogenetic Protein (BMP)—A Study of Periodontal Regenerative Therapy using BMP in Horizontal Bone Defects; Jpn. J. Periodont., vol. 36, 1994; pp. 810-822.

Jarcho, M., Ph.D.; Calcium Phosphate Ceramics as Hard Tissue Prosthetics; J.B. Lippincott Co.; Clinical Orthopaedics and Related Research; Jun. 1981; No. 157; pp. 259-278.

Neo, M. et al.; Differences in ceramic-bone interface between surface-active ceramics and resorbable ceramics: A study by scanning and trasmission electron microscopy; Journal of Biomedical Materials Research, vol.. 26, (1992) pp. 255-267.

* cited by examiner

MATERIAL FOR BONE RECONSTRUCTION

REFERENCE TO RELATED APPLICATION

This application is a 371 of PCT/SE99/01231, filed Jul. 6, 1999, which in turn claims the priority of Sweden 9802529-9 filed 13 Jul. 1998.

The invention relates to a preparation for restoring bone in the body of humans or animals in connection with an existing structure, a bone implant or some other prosthetic construction, as well as a method for restoring bone. The bone restoring preparation is an easily handleable and controllable preparation (composition) adapted to be applied in the position where the bone need be replaced, reinforced or built up, particularly in connection with a bone implant or some other prosthetic construction where the bone volume is insufficient, or where the quality of the bone is too poor to allow a load carrying function, for example permanent fixing of an implant.

By bone implant is in this context meant, for instance, a helical, bone-anchored implant of titanium or a titanium alloy, a so-called fixture, but also comprises other types of implant intended to be installed in bone tissue including bone from humans, especially particulated bone, but also in combination with large cortical and/or spongious bone transplants.

BACKGROUND

Different types of bone grafts have been used more or less successfully to replace lost bone tissue and improve healing of bone defects for the purpose of restoring the function with and without fixed implants. In autogenous transplantation, usually from the patient's own iliac crest, it is among other things the amount of bone and the degree of resorption that affect the result of the treatment. Autologous bone grafting usually requires more than one operation to achieve a satisfactory result and causes considerable postoperative pain to the patient. In homologous bone grafting, use is made of, for instance, demineralised bone matrix from a so-called bone bank. Tissues and structure which have been lost owing to diseases or injuries can today to some extent be replaced by prosthetic constructions which are mechanically fixed to the skeleton. Artificial hips, artificial knee-joints and dental implants are examples of how lost tissue, structure and function can be replaced by this type of construction.

Replacing lost teeth by placing dental implants in the skeleton (jaws) has a high frequency of success provided that there is a sufficient amount of bone of good quality in the close vicinity of and round the implant. After an individually adapted time of healing (3 months–2 years), prosthetic constructions can in most cases be secured to the osseointegrated implants. Some patients have, owing to many years of lack of teeth, obtained impaired conditions than others for obtaining treatment by means of bone-secured implants. It is mainly areas in the upper jaw that have suffered most from bone destruction when the teeth are lost owing to anatomical conditions, but also areas far back in the lower jaw can have a poor quality for implant treatment.

General states of ill-health such as osteoporosis and local defects and lack of bone owing to, for instance, acute injuries, congenital defects, chronical infections or local biological processes such as cysts and tumours in the jaws in most cases affect and may even make treatment with implants impossible if bone is not added or replaced in some way to increase the amount of bone locally round the implants and, thus, the initial stability.

For patients who have been treated with implants and bone replacement materials, it is important to reduce the time of osseointegration and guarantee a higher frequency of success after installation than is possible today. For decades, experiments have been made to replace bone with organic and synthetic materials from different sources, see review, Smiler et al (1992)[1] including resorbable and non-resorbable polymers, bioactive glass, calcium phosphate compounds, calcium carbonates and naturally occurring materials such as cow bone and coral. Transplanting bone from the patient, so-called autograft, is as described above an alternative, but a relatively extensive operation which requires specialist competence, hospital treatment, an extended healing period for the transplant of at least six months and additional inconvenience and pain to the patient. Demineralised freeze-dried bone from a so-called bone bank and spongious bone with mineral from cow bone also result in an extended period of healing, a risk of immunological reactions and infectious states, but also a risk in other aspects including the frequency of success.

There is thus a great need, both with specialists and non-specialists, for being able to apply an easily accessible safe preparation for restoring bone in connection with implant treatment of patients having an insufficient volume of bone and/or too poor bone quality.

An object of the invention is to provide a preparation for restoring bone, which enables implant treatment for patients in various situations especially in areas that otherwise cannot be treated and/or have a poorer prognosis. Calcium phosphate compounds are so-called biocompatible materials, i.e. materials which are mildly reactive with the environment, i.e. promote repair and integration of, for instance, an implant, see Jarcho[2] and Lemons[3]. The commonest form of calcium phosphate compound that is used to stimulate ossification is hydroxylapatite (HA), $Ca_{10}(PO_4)_6(OH)_2$, but also other compounds containing calcium and phosphate ions exist and resemble the inorganic ingredients in skeleton and enamel, see Daculsi et al (1997)[4]. Stoichiometric HA, $Ca_{10}(PO_4)_6(OH)_2$, with a Ca:P ratio of 1.67 is seldom found in vivo. Calcium is to some extent replaced by other ions, such as magnesium, sodium, aluminium, strontium, carbonate, fluorine and chlorine, depending on, inter alia, age, food, sex etc. of the individual. HA may be present in a ceramic and in a non-ceramic form where the degree of crystallinity may vary depending on the temperature at which the calcium phosphate compound is prepared, Ricci et al (1992)[5].

Calcium phosphate compounds such as hydroxylapatite are commercially available and produced by many companies; Impladent Ltd, Holliswood, N.Y., USA, Asahi Optical Co, Ltd, Tokyo, Japan, Interpore Int. and Irvine, Calif., USA. The materials are produced with different properties such as the size of the granules/particles, the degree of resorbability and the chemical composition.

The particles/granules being resorbed do so slowly after application in the bone tissue. It is considered that from the beginning the granules physically take up room in the defect and thus allow an accelerated integrating process compared with an empty defect. While the new bone is forming, mineralising and remodelling, the granules are resorbed slowly for about 3–8 months depending on patient-related factors including the size of the defect and the age of the patient.

There are experimental studies, Hürzeler et al (1995)[6] and Wetzel et al (1995)[7] and clinical studies, Smiler et al (1992)[1], Ricci et al (1992)[5], Judy (1986)[8], Wagner (1989)[9], and Corsair (1990)[10], which demonstrate a certain effect of resorbable granules (Osteogen®) mixed with, for instance, patient blood, common salt or above all in combination with demineralised freeze-dried bone. The possibility of making a filling in sinus maxillaris (sinus of the upper jaw) to increase the possibilities of implant fixing in dogs shows that resorb able HA granules function well and the product is suitable for use to stimulate bone formation round dental implants, Wetzel et al (1995)[7]. However, the granules are mixed with patient blood or common salt, which makes the product difficult to handle. A great drawback of this form/technique of preparation is that it is technically difficult to pass the mass of granules to the defect/cavity area. Having applied the granules, there is a great risk that blood and other body fluids from the area of the wound dilute and transport the material away from the area of application. A further drawback of uncontrolled mixing of, for instance, common salt or the patient's blood is that the risk of contamination of the preparation increases.

Alpher et al (1989)[11] have tried to solve the handling problems. However this reference shows that a mouldable hydroxylapatite preparation based on phospholipids and stearic acid generally does not stimulate the formation of new bone or bone growth, but instead the results indicate a reduction of the bone formation.

Lipids can be divided into different classes. Triglycerides are the most frequent class of lipids and are an important depot of energy in cells. Triglycerides are either built up or decomposed in the body by the intermediary of diglycerides from or into monoglycerides and fatty acids. The body also contains different types of membrane lipids, for example phosphatidyl choline, phosphatidyl ethanolamine, sphingomyelin, cholesterol, mono- and digalactosyldiacylglycerol.

Phospholipids can be prepared fully synthetically but also be cleaned of biological raw materials such as plants or animals. Examples of raw materials are egg yolk, vegetable oils such as soybean oil, rapeseed oil.

It is also preferred for the preparation to contain antioxidants selected according to known principles or naturally occurring. An example of an advantageous antioxidant in this case can be tocopherol. Liposomes consist of a spherical shell of amphiphilic lipids containing an aqueous phase. The potential of the lipid vesicles as carrier of drugs has been studied and described in a number of articles. Huang et al[12] have suggested that negatively charged liposomes can affect the mineralising processes of newly formed bone. This concept was tested in a defect model in miniature swine, however, without any effect. Bone formation between uncoated and liposome-coated calcium phosphate compounds was compared and the uncoated calcium phosphate compounds were surrounded by more bone and riper bone than the liposome-coated ones. In an experimental study by Raggio et al (1986)[13], the authors show that complex acid lipids affect the precipitation of hydroxylapatite mineral in a physiological environment.

Recently some research has focused on the application of introducing exogenic molecules into cells by means of lipid complexes. These new lipids have an important clinical application for drug delivery and gene therapy. Since the lipids can be tailored to have different physical properties, the application may vary, Ashley et al 1996)[14] and Barber et al (1996)[15].

Different systems based on calcium phosphate granules and lipid carriers are described in literature, see for instance EP 0 429 419 which discloses a system where calcium phosphate, especially hydroxylapatite, is used as bone substitute material. In this case, use is made of a monoglyceride-based carrier, which may cause a drawback in implant treatment since preliminary studies indicate that encapsulation may occur, which in turn can have a negative effect on implant integration.

Various systems for the release of pharmaceutical preparations containing bioceramic granules and lipid have also been described in literature, see for instance JP 2,631,890. As examples of different carriers for drugs and molecules that are to be released in bone tissue, mention can be made of collagen, lipids, polymers (for instance PLA/PGA and hyaluronic acid) and ceramics.

A large number of studies demonstrate that mineral deposition in cartilage that is being calcified is only found in vesicles containing phosphatidyl serine and alkaline phosphatase, and that the endocondral calcification process in the growth plate in the epiphysis can be mediated by these. Matrix vesicles and the negatively charged phospholipids therein seem to be involved in the initial formation of calcium hydroxylapatite crystals by way of the interaction between calcium and phosphate ions with phosphatidyl serine in the formation of phospholipid:calcium:phosphate ion complex, Boyan et al (1989)[16].

It is mainly the systemically blood calcium controlling hormones which in different ways control bone cells and, thus, keep the bone mass of the body in equilibrium. In recent years, many studies have been made which indicate that certain biopolymers of the polypeptide type produced by bone cells themselves and/or blood cells from bone marrow or in inflammation after, for instance, trauma, have an important and probably a more immediate importance for activating the individual cells in connection with the bone formation process.

Bone formation and bone resorption are connected to each other. Systemically and locally produced factors control the processes. Many of the growth factors may have different effect on different cells. For instance, PTH and vitamin D can stimulate bone resorption and remodelling by means of the bone-forming cells, cf. Nijweide et al (1986)[17]. On the other hand, the bone-forming cells can be stimulated by TGF beta released of matrix during the bone resorption process, cf. Pfeilschifter et al (1990)[18].

The growth factors and cytokines that are produced by bone cells may have an autocrine or paracrine effect. Examples hereof are: TGF, IGF-I and IFG-II, Beta2 Microglobulin, PDGF and CSFs. Thrombocyte-derived factors such as TGF, PDGF and EGF, but also interleukins, TNFs and Interferon gamma are factors of hematologic origin which have effect on the bone-forming cells. Growth factors which are stored in the bone matrix are the largest reservoir for growth factor activity. The factors stored are, as mentioned above, TGF, IGF-I and IGF-II, Beta2 Microglobulin, PDGF, but also FGF. Bone morphogenetic proteins, BMP, and osteogenine belong to the TGF family. BMP is usually combined with decalcified bone matrix and collagen, cf. Sampath and Reddi (1981)[19] and Saito et al (1994)[20]. Kuboki et al (1995)[21] have proved that BMP induces only bone better if the HA carrier consists of particles which are porous compared with non-porous.

In a newly published experimental study by Urist et al (1997)[22], different systems for administration of the growth factor BMP-2 and its effect on bone formation were investigated. The authors suggest that lipids extracted from bone can function well as a carrier of bone-stimulating peptides in the bone formation process.

Other molecules or ions which can bind strongly to crystal surfaces are, for example, bisphosphonates which can affect osteoblasts and thus dissolution of calcium phosphate compounds in the skeleton, cf. Ebrahimpour et al (1995) 23.

According to the invention, the preparation for restoring bone is a mixture of resorbable calcium phosphate granules and/or a carrier of a biopolymer or lipid type, where the lipid contains an esterified fatty acid selected from the group consisting of triglycerides, diglycerides or phospholipids or combinations thereof. The invention aims at overcoming the difficulties described above and constituting a preparation which easily and in a repetitive manner can be used in connection with bone implants. More specifically, the inventive material is intended to withstand dilution and transporting away from the area of application. Such a mixture can be given the "correct" consistency depending on the type of application, it can be made, for example, mouldable, and it is easy to handle, control and apply.

A desirable weight ratio between calcium phosphate and phospholipid is in the order of 70:15 to 60:40. A desirable weight ratio between phospholipid and water or other water-based liquids is in the order of 1:2 to 10:1, preferably 3:2 to 4:1.

With reference to the water-based liquid that is used to make the preparation mouldable, pure water, an isotonic saline solution or a pharmaceutically acceptable solution are preferred. In some cases when the preparation is being produced in situ, body fluids including blood can be used.

The invention will now be described in more detail in connection with some applications of bone implants where the surrounding bone tissue need to be reinforced and/or built-up, FIG. 1 showing a case where the bone forms a far too loose, load-carrying network, FIG. 2 showing a case where the lateral bone volume is insufficient, FIG. 3 showing a case having angular and/or too narrow bone ridges, FIG. 4 showing a case where the vertical bone height is insufficient, and FIG. 5 being a picture of a preparation applied in rabbit bone.

As mentioned by way of introduction, the preparation for restoring bone consists of a mixture of resorbable calcium phosphate granules and a carrier of a biopolymer or lipid type. To be applied in connection with a bone implant and be kept in the area of application, it is important for the mixture to be mouldable and to have the correct consistency. If the particles are transported away from the area of application, they could cause irritation or complications in other positions in the body.

The calcium phosphate granules should have a Ca/P ratio of between 1 and 2. The granules should have an average diameter of 0.05–5 mm and a micro/macro porosity of 0–80%.

In a study made by Neo et al (1992)[24], the interface between bioactive ceramics and bone was studied by using scanning and transmission electron microscopy. Calcium phosphate granules having an average diameter of 0.1 to 0.3 mm were studied and characterised in respect of resorbability. After 8 weeks, the non-resorbable granules were connected with bone by a thin Ca-P-rich layer consisting of fine apatite crystals, however, different from those in bone in respect of shape, size and orientation. The resorbable granules, however, had direct contact with the bone. The surface of the granules was coarser owing to degradation, and analyses demonstrated that bone grew into the smallest surface irregularities. In another study made by Kitsugi et al[25] four types of calcium phosphate ceramics were compared. The Ca/P ratio was in this case 1, 1.5 and 1.66 and the size of the particles (granules) varied between 0.15 and 0.3 mm. Observations made by transmission electron microscopy showed that the Ca/P ratio did not affect the connection and contact between the particles and the surrounding bone.

According to the invention it is necessary to have a carrier for the resorbable calcium phosphate granules, which may consist of a biopolymer or a lipid containing esters of fatty acids, such a triglyceride, diglyceride, or phospholipids or combinations thereof, for instance some of the lipids described in WO 95/34287.

Preferably, the calcium phosphate granules are distributed in a lamellar, liquid crystalline phase which contains at least one phospholipid and forms either in the body or earlier.

EXAMPLE 1

The following Example describes a test for the handleability of a HA granule/lipid mixture, a phospholipid, (Epikuron 200 supplied by Lucas Mayer) being mixed with HA granules (in this case Apaceram by Pentax) and ethanol, series A samples 1–8. These samples have then been freeze-dried to a constant weight. After freeze-drying, the samples have a composition which is evident from the Table below.

In series B, samples 9–17 have been mixed according to the Table below, whereupon the mouldability has been assessed. The samples were made by 0.9% by weight NaCl in water (physiological salt solution) being weighed and mixed with phospholipid (PC), whereupon hydroxyapatite granules were added. All samples in this series contained 70% by weight of HA and the amount of granules has been kept constant whereas the ratio of phospholipid to water has been varied. The samples that contain only two components PC and granules, as well as water and granules, did not have a satisfactory handleability.

Series A, Samples 1–8

| SAMPLE No. | PC % | HA % | CONSISTENCY |
|---|---|---|---|
| 1 | 10.1 | 89.9 | crumbly |
| 2 | 15.1 | 84.9 | crumbly |
| 3 | 20.1 | 79.9 | crumbly |
| 4 | 25.0 | 75.0 | slightly mouldable |
| 5 | 30.1 | 69.9 | mouldable |
| 6 | 35.1 | 64.9 | mouldable |
| 7 | 40.0 | 60.0 | mouldable |
| 8 | 45.0 | 55.0 | mouldable |

Series B, Samples 9–17

| SAMPLE No. | PC % | 0.9% NACL ISG | HA % | CONSISTENCY |
|---|---|---|---|---|
| 9 | 3.2 | 27.0 | 69.9 | crumbly |
| 10 | 6.0 | 24.0 | 70.0 | crumbly |
| 11 | 9.2 | 20.9 | 69.9 | crumbly, slightly mouldable |
| 12 | 12.0 | 18.1 | 69.9 | crumbly, slightly mouldable |
| 13 | 15.0 | 15.2 | 69.9 | slightly mouldable |
| 14 | 18.0 | 12.0 | 70.0 | mouldable |
| 15 | 21.1 | 9.1 | 69.8 | mouldable |
| 16 | 24.1 | 6.1 | 69.8 | mouldable |
| 17 | 27.0 | 3.0 | 70.0 | crumbly, slightly mouldable |

The weight ratio between the calcium phosphate Component and the lipid and the admixture of water are determined by the requirement that the preparation should be easily handleable and mouldable. Preferably, the weight ratio between calcium phosphate and phospholipid should be within the range 70:15 to 60:40. The weight ratio of phospholipid to water or some other water-based liquid should be in the range 1:2 to 10:1, preferably 3:2 to 4:1.

EXAMPLE 2

Mouldable preparations were produced by mixing 0.21 g phospholipid (1,2-dioleyl-sn-glycero-3-phosphocholine, Avanti Polar Lipids, Inc.) with 0.12 g 0.9% physiological salt solution. After one hour, 0.71 g hydroxyapatite granules (OsteoGen® (HA Resorb)®, Impladent Ltd.) was added. The preparation was mixed to a mouldable consistency and was easy to pack in an applicator.

Figure 5:
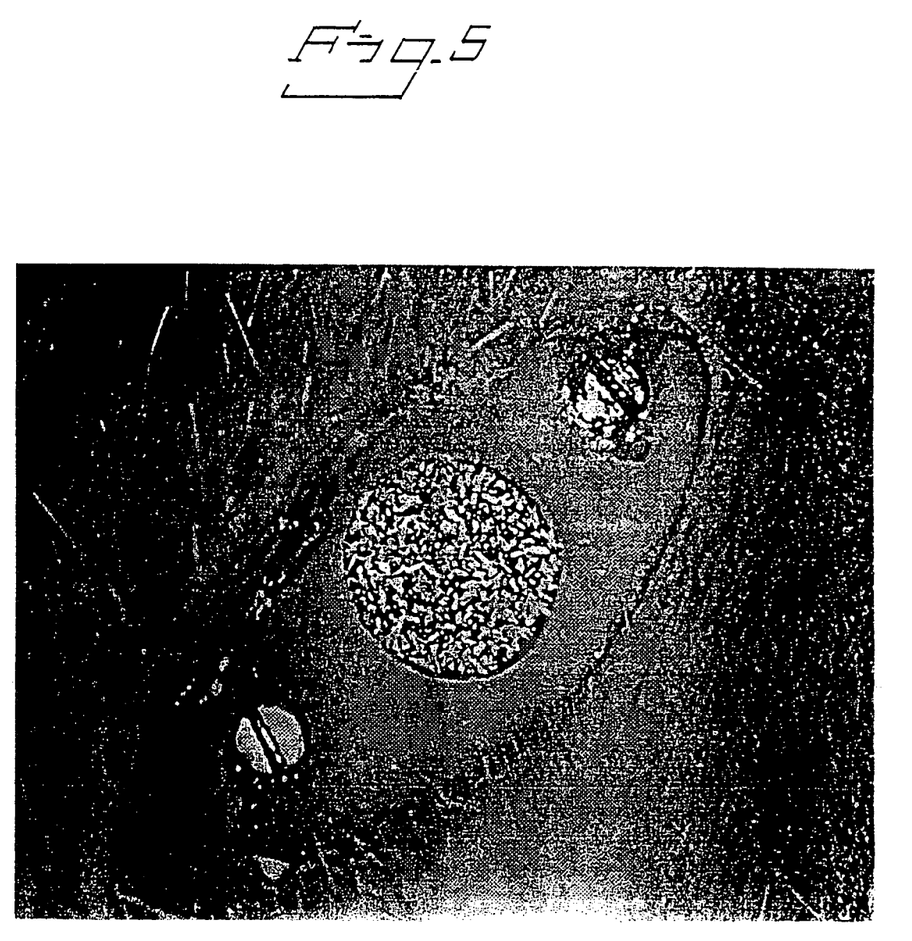

The preparation was evaluated in respect of handleability and applicability in a defect model where circular defects having a diameter of 4 mm had been created in the lower part of the leg (tibia) on adult New Zealand White rabbits. The evaluation shows that the preparation was handleable and easy to apply in the defect area with a modified syringe. The preparation was kept together and was not affected by the relatively strong flow of blood from the area of the wound. FIG. 5 is a picture of the applied preparation inserted in the rabbit bone. An evaluation is now made in respect of the amount of newly formed bone (histomorphometrically) in the defect area, and the result will be compared in pairs with an untreated defect produced in an identical manner.

Instead of a lipid of the type described above, the carrier can consist of a bipolymer, a proteoglycan, a glycoseaminoglycan, for instance hyaluronic acid. Hyaluronic acid is an anionic polysaccharide, composed of repetitive disaccharide units of beta-1-4-glucoronate-beta-1-3-N-acetyl-glucoseamine and is part of the extracellular matrix. Hyaluronic acid serves as lubricant in joints, is present in large quantities in connective tissue and is present in abundance in the eye. In a study investigating whether phagocytable particles of hydroxyapatite have a detrimental effect on bone formation, sodium hyaluronic acid has been used as a carrier solution for hydroxyapatite, cf. Wang J-S et al (1994)[26].

The following formulation of hyaluronic acid and hydroxyapatite can be used as bone substitute material according to the invention. A freeze-dried mixture of sodium hyaluronic acid (Healon®) and hydroxyapatite (65:35% w/w) swells in the presence of water and thus is easy to form and handle. The freeze-dried mixture of sodium hyaluronic acid and hydroxyapatite is easily packed in an applicator and/or a modified syringe, which is rehydrated with water, an aqueous solution or body fluid close to the application so as to form a mouldable hydroxyapatite formulation for restoring bone.

The bone restoring material according to the invention or the granules themselves can advantageously be combined with a cell-stimulating substance which is known per se, for instance growth factors such as BMP and relating to the TGF beta family. Bone-stimulating substances and molecules transmit signals and affect cells and cellular activities in bone. Proteins and polypeptides are examples of substances which have been found to have a bone-stimulating effect in different ways, mainly locally. In addition to the fact that the preparation can be mixed with a bone implant from the patient himself, calcium phosphates granules can be added, containing bone-stimulating substances or parts thereof.

Depending on the properties of the bone-inducing or tissue-promoting factors, some of them exist in an active and an inactive form, respectively, and need be combined with different types of carrier to induce bone and cartilage in vivo. First this was explained by the fact that the growth factor diffused out too fast and was not kept in place sufficiently long for an effect to be achieved. Later studies have proved that the carrier also serves as support and substrate for cells to adhere to and diffuse on since bone formation can occur only on a surface or substrate, cf. Kuboki et al (1995)[21]. Common examples of a carrier for BMP are decalcified bone matrix and collagen, cf. Sampath and Reddi (1981)[19] and Saito et al (1994)[20]. Kuboki et al (1995)[21] have demonstrated that BMP induces only bone if the HA carrier consists of particles that are porous. Tsuruga et al (1997)[27] present theories about cell differentiation and bone formation being strongly dependent on the carrier in its capacity as substrate surface and microenvironment. According to the invention it is thus suggested that the mouldable calcium phosphate granule-lipid mixture is allowed to constitute a carrier for, for example, growth factors.

Figure 1:
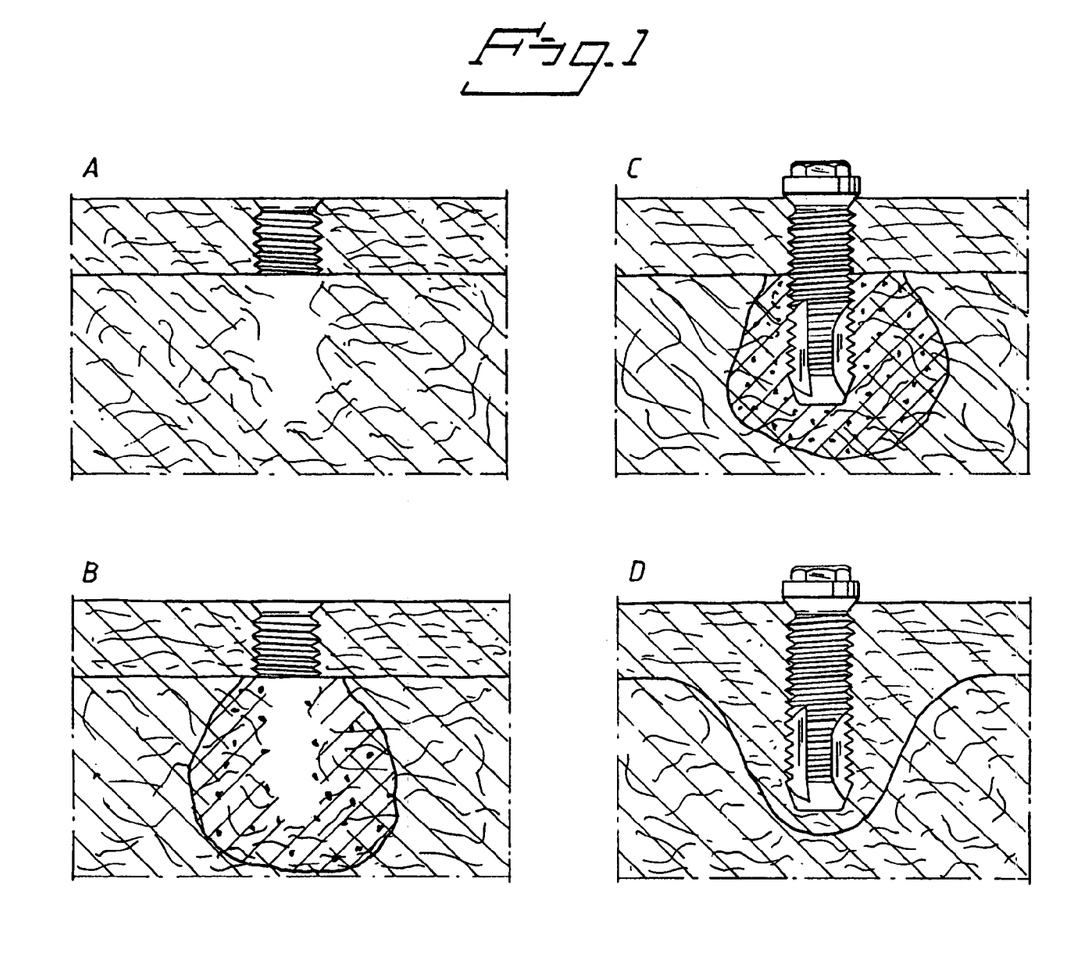

Some examples of situations in which the invention can be applied will be illustrated below with reference to FIGS. 1–4:

FIG. 1

A. After boring (and prethreading) of the bone, B. the preparation is applied in the produced bore by means of a syringe or an inserting appliance. The preparation is pressed against the walls of the cavity and, owing to the bone architecture consisting of no network at all or a loose network, the penetration of the preparation peripherally outwards in the tissue is made possible. C. A helical bone implant (fixture) is installed according to a standard procedure and, after integration, the bone round the fixture has been remodelled and assumed a more lamellar structural appearance and thus is also capable of absorbing loads in a more advantageous manner.

Figure 2:
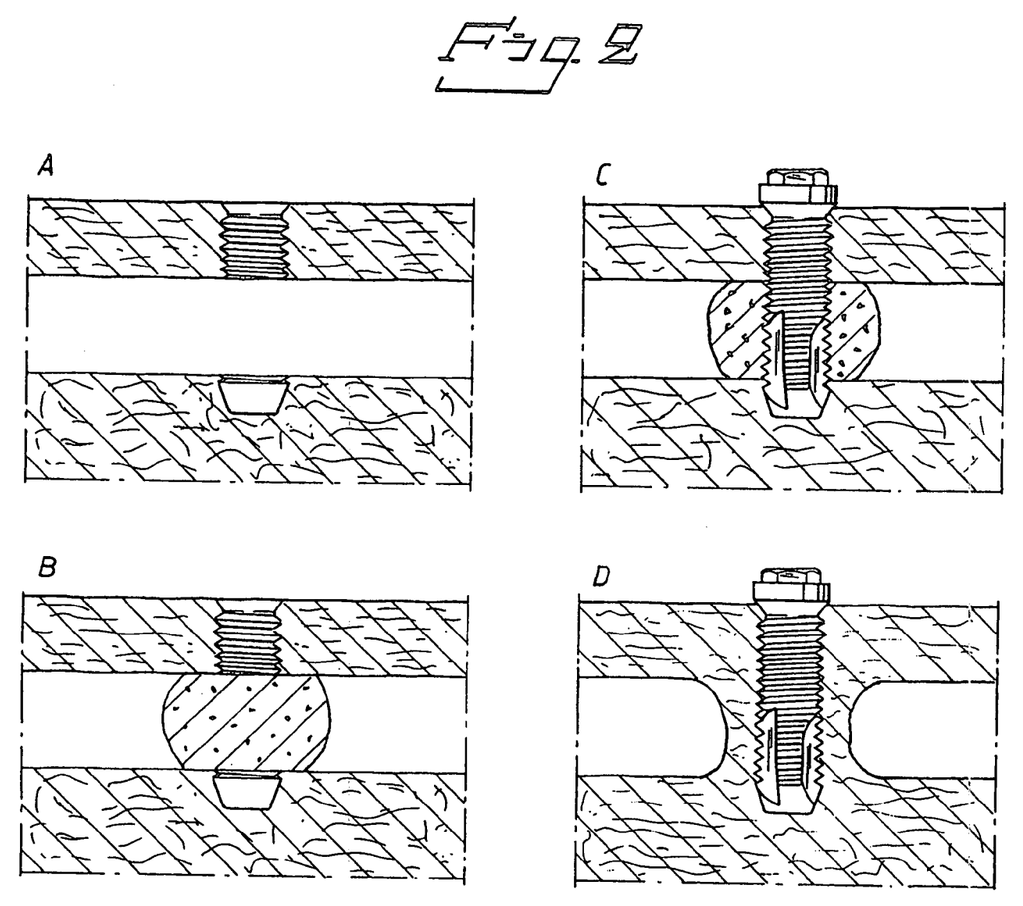

FIG. 2

A. After boring (and prethreading), B. the preparation applied in the produced bore by means of, for instance, a syringe or a similar inserting appliance. The preparation is applied in the defect and, owing to the consistency of the preparation, the granules remain in the application area and thus enable new formation of bone in the defect area. C. The fixture can be installed according to a standard procedure directly by bicortical fixing, D. but also after a short or long period of integration when the bone in the area has been converted and assumed a more lamellar structural and cortical appearance.

Figure 3:
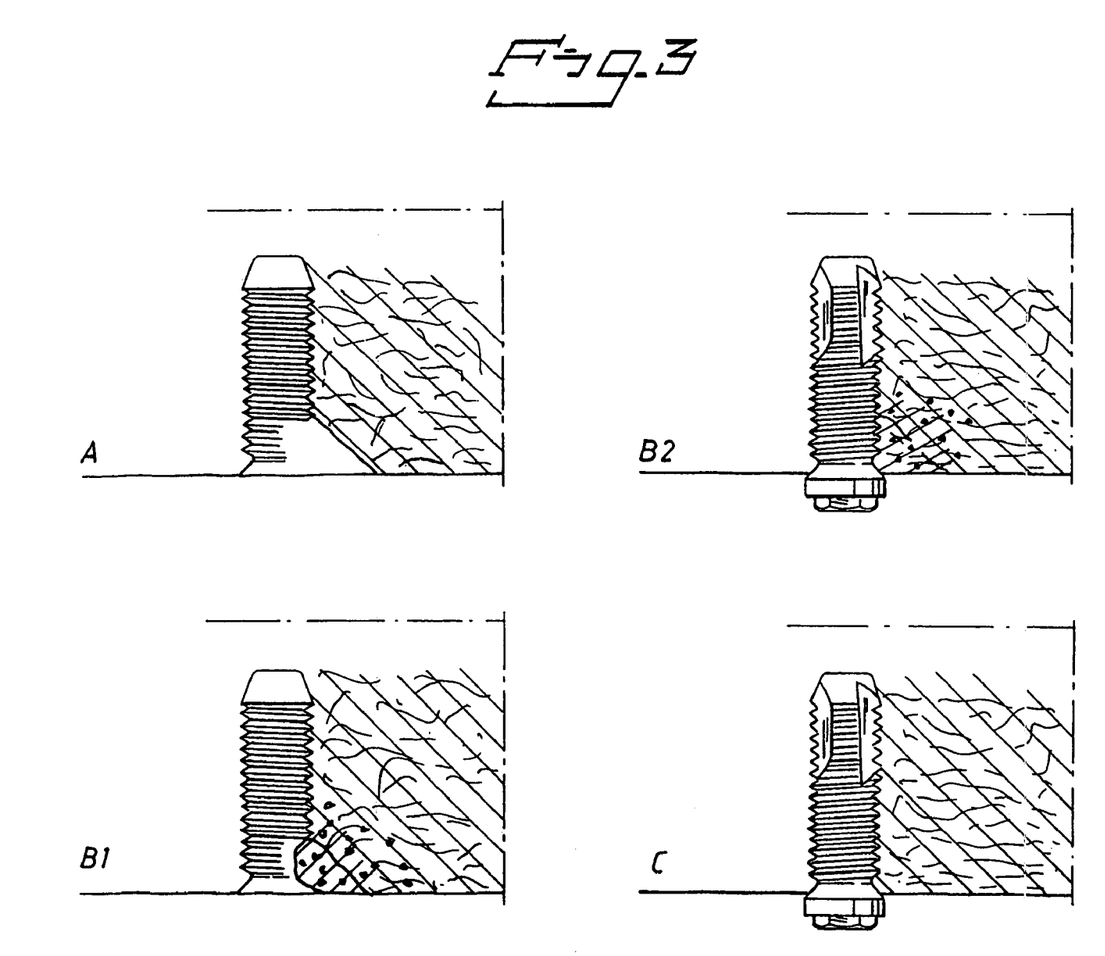

FIG. 3

A. After boring (and prethreading), B1. the preparation is applied before the fixture is installed or B2. after the fixture has been installed in the case of unsatisfactory vertical and horizontal bone volume, for instance angular defects and/or too narrow bone ridges. These two situations are examples of situations where part of the fixture initially does not have a satisfactory contact with the surrounding bone tissue. C. After integrating, the healing process has produced the normal bone architecture in the area.

Figure 4:
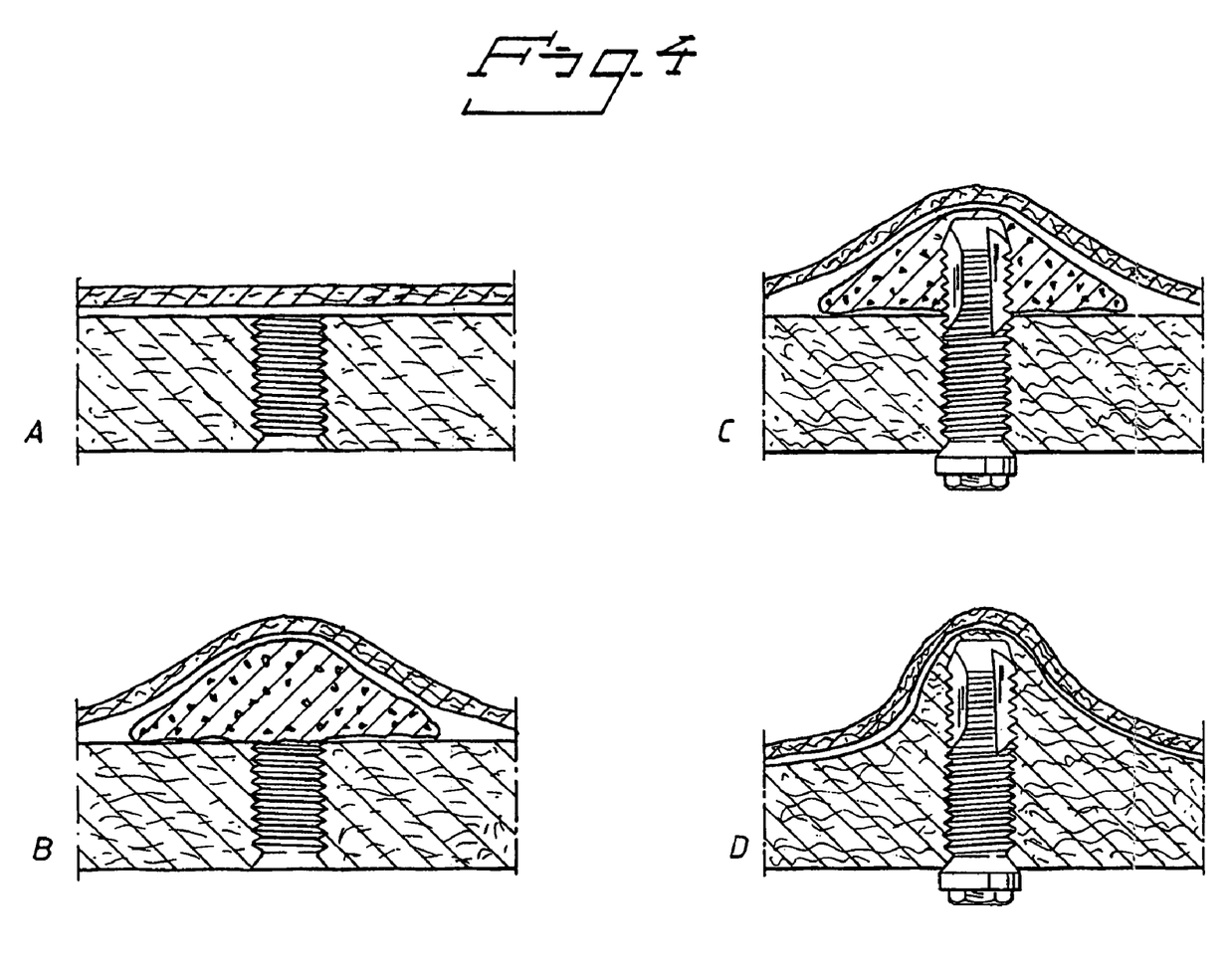

FIG. 4

After toothlessness in the upper jaw, the sinus has in many cases expanded while at the same time the bone ridge has been resorbed. This means that the vertical height that is required for the anchoring of fixtures is insufficient.

Alternative I A. After boring (and prethreading), B. the preparation is applied by means of a modified syringe or some other appliance under the mucous membrane of the sinus. C. The fixture is installed and after unaffected integrating the preparation results in new bone forming in connection with and in contact with the fixture.

Alternative II In a sinus lift, the preparation can also be applied laterally, i.e. communication with the sinus occurs by way of a laterally produced defect, whereupon the mucous membrane of the sinus is lifted and parts of the bottom of the sinus can be filled with the preparation.

FIG. 5

The picture illustrates a preparation according to Example 2 above applied in a rabbit bone, as described above.

The invention claimed is:

1. A bioresorbable and biocompatible composition for restoring bone in the body of a human or other animal said composition comprising:
   calcium phosphate granules;
   lipid; and
   hyaluronic acid;
   wherein said composition forms a moldable, injectable mass upon admixture with water, and
   wherein said composition is resorbable by said body.

2. The composition according to claim 1, wherein the lipid consists of a mixture of esterified glycerol and phospholipid.

3. The composition according to claim 2, wherein the esterified glycerol consists of di- and triglyceride.

4. The composition according to claim 2, wherein the esterified glycerol is a diester.

5. The composition according to claim 2, wherein the esterified glycerol is a triester.

6. The composition according to claim 1, wherein said lipid comprises a mixture of phospholipids.

7. The composition according to claim 6, wherein the phospholipid is a sphingomyeline.

8. The composition according to claim 6, wherein the phospholipid is a phosphatidyl choline.

9. The composition according to claim 1, wherein the lipid is prepared from a vegetable oil or egg yolk.

10. The composition according to claim 1, wherein the lipid consists of at least one phospholipid and a water-based liquid as carrier.

11. The composition according to claim 10, wherein the lipid is in a lamellar floating crystalline phase.

12. The composition according to claim 10, wherein the weight ratio between lipid and water-based liquid is in order of 1:2 to 10:1.

13. The composition according to claim 10, wherein the weight ratio between lipid and water or some other water-based liquid is in the order of 3:2 to 4:1.

14. The composition according to claim 1, further comprising glycoseaminoglycan.

15. The composition according to claim 14, wherein said glycoseaminoglycan comprises hyaluronic acid.

16. The composition according to claim 15, wherein said composition consists of a free-flowing mixture of sodium hyaluronic acid and calcium phosphate granules which can be packed and then rehydrated in connection with use.

17. The composition according to claim 1, wherein the calcium phosphate granules have a Ca/P ratio which is between 1 and 2.

18. The composition according to claim 17, wherein the calcium phosphate granules contains hydroxyapatite of the form $Ca_{10}(PO_4)_6(OH)_2$.

19. The composition according to claim 17, wherein the calcium phosphate granules are selected from the group consisting of dicalcium phosphate dihydrate, octacalcium phosphate, tricalcium phosphate and hydroxyapatite.

20. The composition according to claim 17, wherein the calcium phosphate granules further comprises materials selected from the group consisting of magnesium, fluorine and carbonate ions.

21. The composition according to claim 17, wherein the calcium phosphate granules have a diameter in the order of 0.05 to 5 mm.

22. The composition according to claim 17, wherein the calcium phosphate granules have a porosity of 0–80%.

23. The composition according to claim 1, wherein the weight ratio between the calcium phosphate granules and the lipid is in the order of 70:15 to 60:40.

24. The composition according to claim 1, further comprising biologically-active factors selected from the group consisting of tissue-promoting factors, factors which inhibit decomposition of tissue, and growth factors.

25. The composition according to claim 1, wherein the tissue-promoting factor is added wholly or partially.

26. The composition according to claim 25, wherein said tissue-promoting factor is a fragment thereof wherein said fragment retains biological activity.

* * * * *